US012109163B2

(12) United States Patent
Podhorsky et al.

(10) Patent No.: US 12,109,163 B2
(45) Date of Patent: Oct. 8, 2024

(54) DEVICE FOR TREATMENT OF THE PEYRONIE'S DISEASE

(71) Applicants: MEDIPO—ZT, s.r.o., Husovice (CZ); CESKE VYSOKE UCENI TECHNICKE V PRAZE, Dejvice (CZ)

(72) Inventors: Jaroslav Podhorsky, Husovice (CZ); Jiri Podhorsky, Husovice (CZ); Sarka Peskova, Vokovice (CZ); Vladimir Kristek, Ruzyne (CZ); Miroslav Petrtyl, Zabehlice (CZ); Petr Konvalinka, Vrsovice (CZ); Pavel Drlik, Miskovice (CZ); Jiri Litos, Holesovice (CZ); Martin Valek, Chodov (CZ)

(73) Assignees: MEDIPO—ZT, s.r.o, Husovice (CZ); CESKE VYSOKE UCENI TECHNICKE V PRAZE, Dejvice (CZ)

( * ) Notice: Subject to any disclaimer, the term of this patent is extended or adjusted under 35 U.S.C. 154(b) by 955 days.

(21) Appl. No.: 17/133,970

(22) Filed: Dec. 24, 2020

(65) Prior Publication Data
US 2021/0196561 A1    Jul. 1, 2021

(30) Foreign Application Priority Data
Dec. 27, 2019   (CZ) ................. CZ2019-801

(51) Int. Cl.
*A61H 19/00* (2006.01)
*A61H 23/00* (2006.01)
(52) U.S. Cl.
CPC ........... *A61H 19/32* (2013.01); *A61H 23/008* (2013.01); *A61H 2023/002* (2013.01);
(Continued)

(58) Field of Classification Search
CPC .................. A61H 19/32; A61H 23/008; A61H 2023/002; A61H 2201/0107;
(Continued)

(56) References Cited

U.S. PATENT DOCUMENTS 10,441,499 B1 * 10/2019 Zhu ........................ G10K 15/06
2012/0215142 A1 * 8/2012 Spector .............. A61B 17/2251
601/46
(Continued)

FOREIGN PATENT DOCUMENTS

EP         1591070 A1    11/2005
WO    2011051928 A1     5/2011

OTHER PUBLICATIONS

Czech Republic Search Report dated Apr. 27, 2020.

*Primary Examiner* — Sanjay Cattungal
(74) *Attorney, Agent, or Firm* — Panitch Schwarze Belisario & Nadel LLP

(57) ABSTRACT

A device for treatment of the Peyronie's disease, containing a hollow cylindrical body placed in the bed of a fixed base plate for precision positioning of the penis with respect to the center of the plaque in its subcutaneous tissue, wherein adjacent to the cylindrical body is the face of the shock wave generator firmly connected to a supporting rigid navigation frame with the possibility of travel in three mutually orthogonal directions and three rotations in three mutually perpendicular planes to ensure the localization of the highest shock wave energy level in the second focal point of the shock wave generator which is identical to the position of the center of the plaque, and the space between the inner and outer walls of the cylindrical body is filled with degassed water with a temperature close to the patient's temperature.

7 Claims, 1 Drawing Sheet

(52) U.S. Cl.
CPC ............... *A61H 2201/0107* (2013.01); *A61H 2201/0242* (2013.01); *A61H 2201/169* (2013.01); *A61H 2201/5007* (2013.01); *A61H 2201/5025* (2013.01); *A61H 2201/5043* (2013.01)

(58) Field of Classification Search
CPC ...... A61H 2201/0242; A61H 2201/169; A61H 2201/5007; A61H 2201/5025; A61H 2201/5043; A61H 2205/087; A61B 17/225; A61B 17/2251; A61B 17/2255; A61B 2017/00876
See application file for complete search history.

(56) References Cited

U.S. PATENT DOCUMENTS

2017/0296209 A1\* 10/2017 Morganstern ...... A61K 41/0028
2020/0093857 A1\* 3/2020 Morganstern ........ A61K 31/522

\* cited by examiner

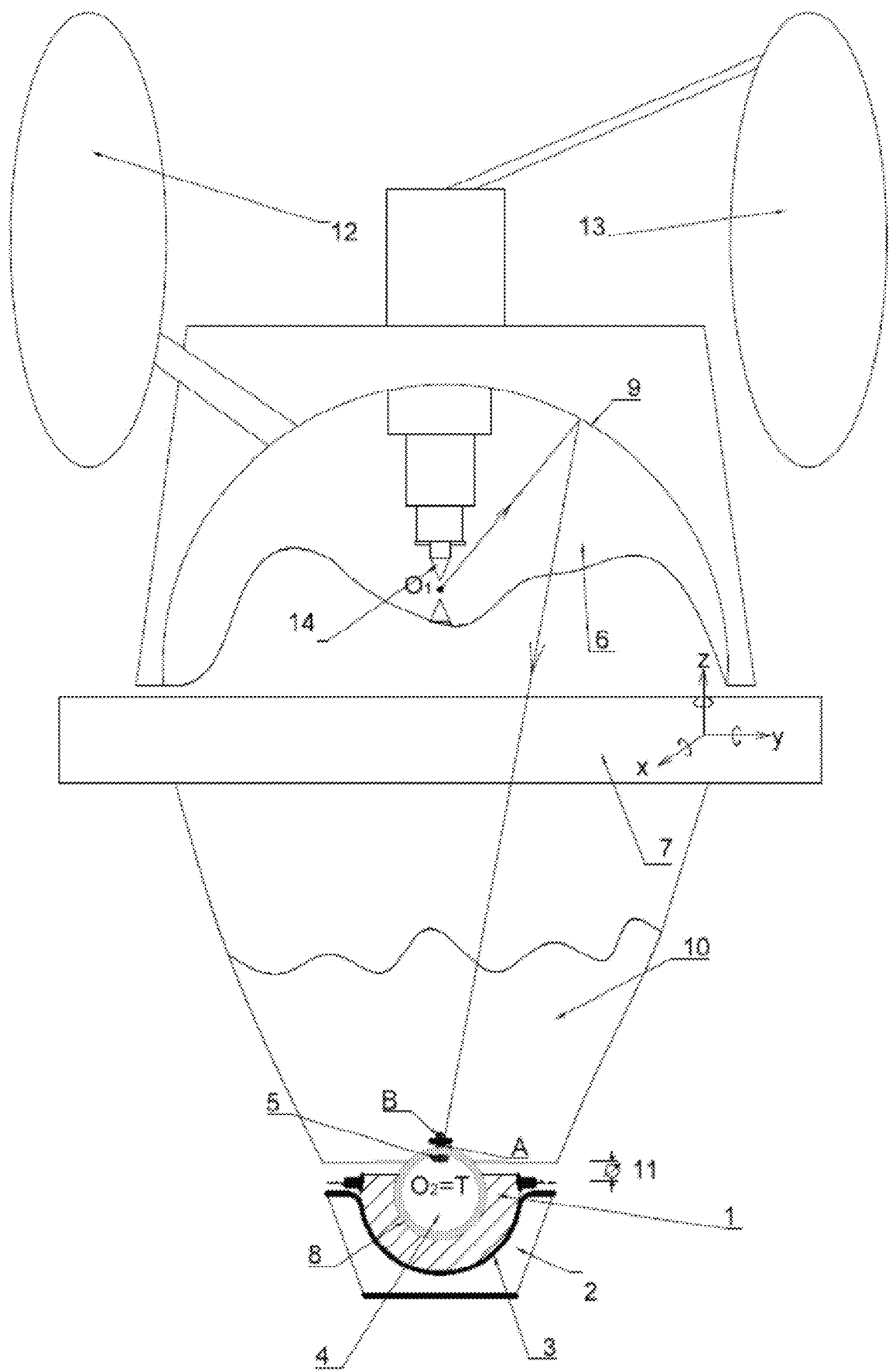

DEVICE FOR TREATMENT OF THE PEYRONIE'S DISEASE

FIELD OF THE INVENTION

The present invention relates to the effective non-invasive treatment of Peyronie's disease by a new device comprising an aiming and fixing element that stabilizes the penis and allows the second focal point of the shock wave generator to be accurately oriented and the maximum shock wave energy directed to the center of the fibrous plaque.

BACKGROUND OF THE INVENTION

At present, shock wave generators are used in urological clinics for the destruction of concretions, i.e. stones, in the kidneys and gallbladder, urinary tract and bile ducts. The shock waves originate in the shock wave generator. In electro-hydraulic applicators, the shock wave propagates in the hydraulic medium as a radial wave towards the reflector. Each beam of the shock wave bounces off it, passing through the hydraulic medium, the rubber bag, the contact gel, into the tissues, and within them up to the secondary focal point, which for therapeutic efficacy must be identical to the point of application of the shock wave energy, i.e. the center of the plaque. The Peyronie's disease manifests itself by the occurrence of a rigid scar, the so-called fibrous plaque, with various subsequent manifestations like excessive curvature of the penis centerline, its local deformations, painful erection, its shortening etc. The current state of therapy is based either on conservative methods, in particular the administration of drugs, or on an invasive method—surgery, accompanied by pain and with uncertain outcome. The method of application of a focused, i.e. targeted, shock wave with the application of an aiming and fixing device is considered to be a conservative therapy during which no pain occurs.

SUMMARY OF THE INVENTION

The above drawbacks are overcome by using the device for treating Peyronie's disease according to the present invention. Its principle is that it comprises a hollow cylindrical body located in the bed of a fixed base plate for precise positioning of the penis with respect to the center of the plaque in its subcutaneous tissue. Adjacent to the cylindrical body is the face of the shock wave generator firmly connected to a supporting rigid navigation frame with the possibility of travel in three mutually orthogonal directions and three rotations in three mutually perpendicular planes to ensure the localization of the highest shock wave energy level in the second focal point O2 of the shock wave generator which is identical to the position of the center T of the plaque. The space between the inner and outer walls of the cylindrical body is filled with degassed water with a temperature close to the patient's temperature.

The hollow cylindrical body may be formed by a symmetrical or asymmetrical hollow ring or tube and is preferably made of an elastic material selected from the group of bio-compatible polymer, rubber, composite material. The hollow cylindrical body is preferably provided with a water valve for letting the water in/out of the interior of the hollow cylindrical body and a manual and/or software control of the hydraulic pressure.

The hollow cylindrical body can be connected to the base plate by a bond selected from the group consisting of mechanical, magnetic and electromagnetic. The inner contact surface of the hollow cylindrical body is preferably provided with a layer of contact gel at the points of contact with the penis.

In a preferred embodiment, the device is provided with an optical indicator of the position of the second focal point O2 and a device for measuring the magnitude of displacements of the distance of the center T from the point of contact of the cylindrical body with the face of the shock wave generator.

The improvement of the transmission and efficiency of shock energy to the application point is provided by a comprehensive aiming and fixing device for precisely targeted shock energy transfer and for penis stabilization—AFD (hereinafter AFD). AFD is either part of an electrohydraulic shock wave applicator for the destruction of concretions in the kidneys and gallbladder, urinary and biliary tracts, or a special device only for the treatment of Peyronie's disease.

The aforementioned shortcomings of invasive surgery, or the low efficacy of drug therapy in the treatment of Peyronie's disease are eliminated by the provision of the AFD aiming and fixation device that directs the shock energy and stabilizes the penis. AFD is characterized by the application of a focused shock wave generated by a spark gap in an aquatic environment and is part of a spheroidal reflector. The spark gap located in the first focal point of the spheroidal reflector generates a shock wave during the high voltage discharge, which is reflected from the inner walls of the spheroid and directed towards the second focal point. In the second focal point, on the outside of the spheroid, the shock wave energy is concentrated in the center of the fibrous plaque. The second focal point is the place of effect of the maximum shock wave energy. The aquatic environment for the formation of a high-voltage discharge in the spark gap forms an integral part with the open spheroid and the water in the space enclosed by the flexible bag.

Fixation of the penis using the AFD in relation to the treated tissue in the second focal point of the spheroidal reflector is provided by a holder with fixation elements. The optical indicator determines the position of the second focal point. For the AFD function, the device is connected to a shock wave generator and a water treatment plant. The patient, the treated tissue and the AFD, according to the following indicators, are fixed to each other with the possibility of changing position.

The aiming and fixing device for transfer of the shock energy and for stabilization of the penis during application of the focused shock wave for clinical treatment of the Peyronie's disease allows and ensures propagation of the shock wave in the aquatic environment of the generator, and furthermore in the aquatic environment of the ring/tubular penis wrappings, in body fluids in the subcutaneous tissue and in the plaques in the penis. The advantage is the targeting of the shock force to the centers of the plaques in the penis while regulating the energy of the shock waves and regulating the distance of the electrodes in the spark gap of the shock wave generator.

The second focal point is identical with the place of effect of the maximum shock wave energy. Another advantage is the possibility to apply a control optical indicator of the position of the second focal point and, to change the geometric parameters of the spheroid, or to regulate the distance of the second focal point from the center of the plaque in the penis. The solution allows the AFD to be connected to an existing external water treatment plant for hydraulic pressure rings/hydraulic pressure tubes applied around the penis and also to the shock wave generator.

The subject of the patent is the aiming and fixing device AFD, which forms part of a medical device (MD) for treatment of the Peyronie's disease. MD uses the energy of a focused, i.e. targeted, shock wave, which is applied through the AFD to the location of the fibrous plaque in the penis. The AFD stabilizes the penis and allows the second focal point of the shock wave generator to be accurately oriented and the maximum shock wave energy directed to the center of the fibrous plaques.

The application of a focused shock wave with the application of the AFD is considered to be a conservative therapy during which no pain occurs.

CLARIFICATION OF DRAWINGS

The device for treatment of the Peyronie's disease according to the present invention will be illustrated on a specific example of embodiment using the attached drawing (FIG. 1) showing the embodiment schematic.

EXAMPLES OF INVENTION EMBODIMENTS

The example AFD embodiment is formed by a one-piece or multi-piece symmetrical or asymmetrical cylindrical body in the shape of a hollow ring 1a, or a tube 1b with a hollow wall for placement of the penis 4, which are made of an elastic material, for example a bio-compatible polymer, rubber, composite material, etc. The space between the inner and outer wall surfaces of the wider ring 1a or the shorter tube 1b are filled with degassed water with a temperature close to the patient's temperature. The AFD is capable of letting the water in/out of the interior of the ring 1a or the short tube 1b and measure and externally regulate the hydraulic pressure. The water pressure in the ring 1a or the tube 1b can be thus externally controlled either manually or by software. To the hollow ring 1a, or tube 1b there is a shock wave generator 6 attached, which is fixed to the support rigid navigation frame 7 which can travel in three orthogonal directions and rotate in three orthogonal panes.

The hollow ring 1a or tube 1b with a hollow wall are bound to a stable base, for example to a base plate 2 that eliminates the patient's movements. In the base plate 2 there is the bed 3 for precision positioning of the penis 4 with respect to the center of the plaque 5 in its subcutaneous tissue. The AFD has a fixating adjustable ring 1a or a fixating adjustable tube 1b, that is mechanically or magnetically or electro-magnetically firmly bound to the base plate 2. Point B, situated in the center of the flat segment of the shock wave generator 6 face, is identical with point A situated on the surface of the cylindrical body wrapping around the penis 4. In use, the identity of points A and B must be achieved manually or mechatronically, and at the same time the identity of the second focal point O2 of generator 6 with the center T of plate 5 must be achieved.

The wide ring 1a or shorter tube 1b have an inner contact surface in the points of contact with the penis 4, coated with a layer of contact gel 8.

Penis 4 is firmly bound to the base plate 2 and furthermore, at point A on the surface of ring 1a or tube 1b it is in contact with point B, situated in the center of the flat surface of the face of the shock wave generator 6. The AFD provides the localization of the highest energy level of the shock wave in the second focal point O2 of shock wave generator 6, which is identical with the position of the center T of the plaque 5.

The AFD has an optical indicator of the position of the second focal point O2. The AFD allows to measure the distance of points TA, or TB, manually or with and additional electronic device for measuring lengths/displacements.

Fixation of the penis 4 using the AFD in relation to the treated tissue in the second focal point O2 of the spheroidal reflector is provided by a holder with fixation elements. The optical indicator determines the position of the second focal point O2. For the AFD function, the device is connected to a shock wave generator 6 and a water treatment plant. The patient, the treated tissue and the AFD are fixed to each other with the possibility of changing position.

The aiming and fixing device for transfer of the shock energy and for stabilization of the penis 4 during application of the focused shock wave for clinical treatment of the Peyronie's disease allows and ensures propagation of the shock wave in the aquatic environment of the generator, and furthermore in the aquatic environment of the ring/tubular penis wrappings, in body fluids in the subcutaneous tissue and in the plaques in the penis. The advantage is the targeting of the shock force to the centers of the plaques in the penis while regulating the energy of the shock waves and regulating the distance of the electrodes in the spark gap of the shock wave generator.

The second focal point is identical with the place of effect of the maximum shock wave energy. Another advantage is the possibility to apply a control optical indicator of the position of the second focal point, and to change the geometric parameters of the spheroid, or to regulate the distance of the second focal point from the center of the plaque in the penis. The solution allows the AFD to be connected to an existing external water treatment plant for hydraulic pressure rings/hydraulic pressure tubes applied around the penis and also to the shock wave generator.

The subject of the patent is thus the aiming and fixing device AFD, which forms part of a medical device (MD) for treatment of the Peyronie's disease. MD uses the energy of a focused, i.e. targeted, shock wave, which is applied through the AFD to the location of the fibrous plaque in the penis. The AFD stabilizes the penis and allows the second focal point of the shock wave generator to be accurately oriented and the maximum shock wave energy directed to the center of the fibrous plaques.

The application of a focused shock wave with the application of the AFD is considered to be a conservative therapy during which no pain occurs.

INDUSTRIAL APPLICABILITY

The application of a focused shock wave with the device herein may be considered to be a conservative therapy during which no pain occurs.

The invention claimed is:

1. A device for treatment of the Peyronie's disease of a penis, the device comprising:
   a shock wave generator firmly connected to a supporting rigid navigation frame, wherein the navigation frame is moveably supported in three mutually orthogonal directions and in three rotations in three mutually perpendicular planes to ensure the localization of the highest shock wave energy level of a shock wave generated by the shock wave generator in a second focal point of the shock wave generator which is identical to the position of a center of a plaque in the subcutaneous tissue of a penis to be treated; and
   a hollow cylindrical body for receiving a penis to be treated, wherein the hollow cylindrical body comprises an inner and an outer wall which define a space, wherein the hollow cylindrical body is formed by a tube having a hollow wall, wherein the hollow cylindrical body is placed in a bed of a fixed base plate for precision positioning of the penis to be treated with respect to the center of a plaque in its subcutaneous tissue, wherein adjacent to the hollow cylindrical body is a face of the shock wave, and wherein the space between the inner and outer walls of the cylindrical body is filled with degassed water with a temperature close to the patient's temperature.

2. The device according to claim 1, wherein the hollow cylindrical body is made of an elastic material selected from the group of bio-compatible polymer, rubber, composite material.

3. The device according to claim 1, wherein the hollow cylindrical body is provided with a water valve for letting the water in/out of the space defined by the inner and outer wall of the hollow cylindrical body and a manual and/or software control of the hydraulic pressure.

4. The device according to any of claim 1, wherein the hollow cylindrical body is connected to the base plate by a bond selected from the group consisting of mechanical, magnetic and electromagnetic.

5. The device according to claim 1, wherein the hollow cylindrical body is coated with a layer of contact gel at the points of contact with the penis received in the hollow cylindrical body.

6. The device according to claim 1, comprising an optical indicator of the position of the second focal point of the shock wave generator.

7. The device according to claim 1, comprising a device for measuring the magnitude of displacements of the distance of the center from the point contact of the hollow cylindrical body with the face of the shock wave generator.

* * * * *